(12) United States Patent
Bhadra et al.

(10) Patent No.: US 11,510,628 B2
(45) Date of Patent: Nov. 29, 2022

(54) ELIMINATION OF ARTIFACTS DUE TO DELIVERY OF AN ELECTRICAL SIGNAL FROM NEURAL RECORDINGS

(71) Applicant: Case Western Reserve University, Cleveland, OH (US)

(72) Inventors: Niloy Bhadra, Richmond Heights, OH (US); Kevin L. Kilgore, Avon Lake, OH (US); Thomas Eggers, Cleveland Heights, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 592 days.

(21) Appl. No.: 16/585,214

(22) Filed: Sep. 27, 2019

(65) Prior Publication Data

US 2020/0100731 A1 Apr. 2, 2020

Related U.S. Application Data

(60) Provisional application No. 62/737,961, filed on Sep. 28, 2018.

(51) Int. Cl.
*A61N 1/36* (2006.01)
*A61B 5/00* (2006.01)
*A61B 5/24* (2021.01)
*A61B 5/389* (2021.01)

(52) U.S. Cl.
CPC .............. *A61B 5/7217* (2013.01); *A61B 5/24* (2021.01); *A61B 5/389* (2021.01); *A61N 1/36139* (2013.01)

(58) Field of Classification Search
CPC ......... A61B 5/7217; A61B 5/24; A61B 5/389; A61B 5/686; A61B 5/377; A61B 5/291; A61B 5/4035; A61B 5/4094; A61B 5/294; A61B 5/311; A61B 5/4064; A61N 1/36139
See application file for complete search history.

(56) References Cited

U.S. PATENT DOCUMENTS

| | | | |
|---|---|---|---|
| 2007/0270918 A1* | 11/2007 | De Bel | A61B 5/30 607/48 |
| 2012/0203296 A1* | 8/2012 | Lisogurski | A61N 1/0492 607/17 |
| 2016/0331326 A1* | 11/2016 | Xiang | A61B 5/24 |

* cited by examiner

*Primary Examiner* — Carl H Layno
*Assistant Examiner* — Anh-Khoa N Dinh
(74) *Attorney, Agent, or Firm* — Tarolli, Sundheim, Covell & Tummino LLP

(57) ABSTRACT

Artifacts due to delivery of an electrical signal (e.g., for neural stimulation or nerve block) can be eliminated from neural recordings. An activating stimulus (AS) can be applied by at least one neural electrode located at a first position within a body or a preparation proximal to a neural structure. The AS includes an electrical waveform configured to affect (e.g., stimulate or block) conduction in the neural structure. A counter stimulus (CS) can be applied by at least one electrode located at a second position within the body or the preparation remote from the neural structure. The CS includes an electrical waveform configured with a timing parameter and an amplitude parameter selected based on a feature of the AS. Artifacts due to the AS can be blocked by the CS during the neural recordings.

16 Claims, 5 Drawing Sheets ical signal.
ELIMINATION OF ARTIFACTS DUE TO DELIVERY OF AN ELECTRICAL SIGNAL FROM NEURAL RECORDINGS

RELATED APPLICATIONS

This application claims priority to U.S. Provisional Application Ser. No. 62/737,961, filed Sep. 28, 2018, entitled "ELIMINATION OF STIMULATION AND ELECTRICAL NERVE BLOCK ARTIFACTS IN NEURAL RECORDINGS". The entirety of this provisional application is hereby incorporated by reference for all purposes.

GOVERNMENT SUPPORT

This invention was made with government support under R01-EB-024860 awarded by the National Institutes of Health (NIH), National Institute of Biomedical Imaging and Bioengineering (NIBIB). The government has certain rights in this invention.

TECHNICAL FIELD

The present disclosure relates generally to neural recording and, more specifically, to systems and methods to eliminate artifacts due to delivery of an electrical signal (e.g., for neural stimulation or nerve block) from neural recordings.

BACKGROUND

Neural signals can be acquired from nerves, muscles, or the central nervous system in the form of recordings, like electroneurograms (ENGs) or electromyograms (EMGs). Some of these recordings are obtained as the response to deliberate application of an electrical signal (e.g., configured for neural stimulation or nerve block) to one or more neural structures; but the recorded signal can be distorted by a stimulus artifact due to interference with the recording and saturation of the amplifiers caused by the application of the electrical signal.

There are two classical approaches for dealing with this artifact. The first uses amplifier blanking to ensure that the amplifier does not get saturated with a downside of the loss of signal during the blanking period. The second approach uses post-hoc data manipulation to minimize the noise by using digital filtering techniques. However, since the signal of interest is completely lost during the duration of the stimulation artifact and partially lost during the recovery of the amplifier, it is impossible to retain all the information.

Summary

The present disclosure relates to systems and methods to eliminate artifacts due to delivery of an electrical signal (e.g., for neural stimulation or nerve block) from neural recordings. As opposed to classical approaches, the systems and methods of the present disclosure do not require a blanking period and do not need to perform post-hoc data manipulation.

In another aspect, the present disclosure can include a system that can eliminate artifacts due to delivery of an electrical signal (e.g., for neural stimulation or nerve block) from neural recordings. The system can include at least one at least one waveform generator configured to generate an activating stimulus (AS), comprising a first electrical waveform comprising a feature, and a counter stimulus (CS), comprising a second electrical waveform configured with a timing parameter and an amplitude parameter selected based on the feature of the AS. The system can also include at least one neural electrode coupled to the at least one waveform generator to receive the AS and configured to be placed in a first position within a body or a preparation proximal to a neural structure to deliver the AS to the neural structure to affect conduction in the neural structure; and at least one electrode coupled to the at least one waveform generator to receive the CS and configured to be placed in a second position within the body or the preparation remote from the neural structure to deliver the CS to the second position. The system can also include a recording device comprising a recording electrode configured to be placed at a third position within the body or the preparation to receive electrical potentials from the neural structure, wherein the third position is near the second position and wherein the CS counteracts an artifact caused by the AS at the third location.

In a further aspect, the present disclosure can include a method for eliminating artifacts due to delivery of an electrical signal (e.g., for neural stimulation or nerve block) from neural recordings. The method includes applying an activating stimulus (AS), by at least one neural electrode located at a first position within a body or a preparation proximal to a neural structure. The AS includes an electrical waveform configured to affect conduction in the neural structure. The method also includes applying a counter stimulus (CS), by at least one electrode located at a second position within the body or the preparation remote from the neural structure. The CS includes an electrical waveform configured with a timing parameter and an amplitude parameter selected based on a feature of the AS. The method also includes receiving, by a recording electrode located at a third position (near the second position) within the body or the preparation, electrical potentials from the body or the preparation. The CS counteracts an artifact caused by the AS at the third location

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
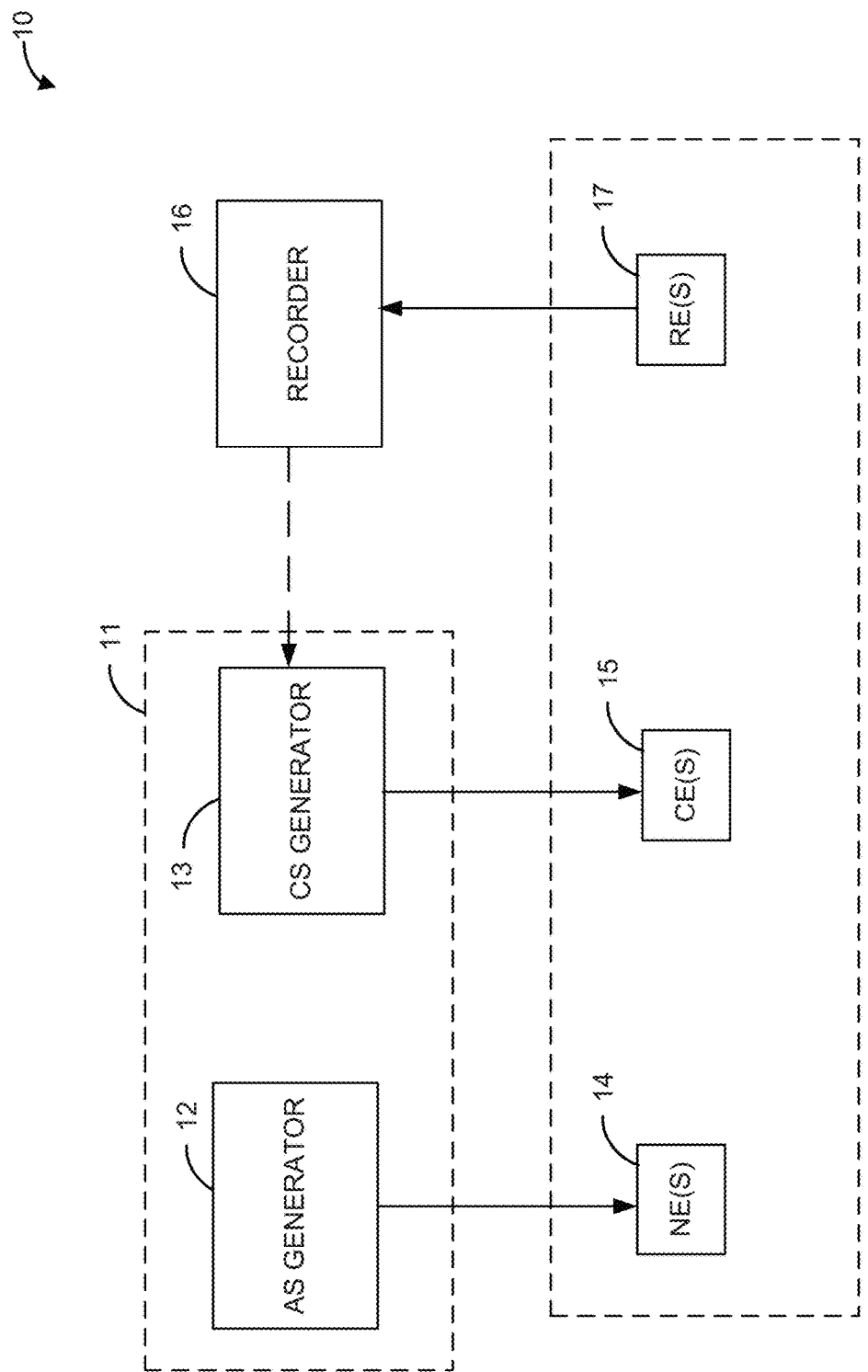
FIG. 1 is a schematic diagram showing an example of a system that can eliminate artifacts due to delivery of an electrical signal (e.g., for neural stimulation or nerve block) from neural recordings in accordance with an aspect of the present disclosure.

Unless otherwise defined, all technical terms used herein have the same meaning as commonly understood by one of ordinary skill in the art to which the present disclosure pertains.

As used herein, the singular forms "a," "an" and "the" can also include the plural forms, unless the context clearly indicates otherwise.

As used herein, the terms "comprises" and/or "comprising," can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

As used herein, the terms "first," "second," etc. should not limit the elements being described by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "neural recording" can refer to a measurement of a local voltage at a recording site. The neural recording can be made by a recording electrode to convey information about activity (e.g., conduction) of one or more neural structures. For example, neural recordings can include electroneurograms (ENGs), electromyograms (EMGs), or the like.

As used herein, the term "artifact" can refer to a phenomena that corrupts a measurement. In some instances, the artifact can be a stimulation artifact due to application of an electrical signal to deliver stimulation to a neural structure (e.g., for stimulation or block).

As used herein, the term "neural structure" can refer to one or more conductive cells or tissues that are part of and/or innervated by the nervous system. A neural structure can be, for example, one or more nerves, one or more central nervous system cells, one or more muscle fibers, and the like.

As used herein, the term "eliminate" can mean remove something. Eliminated can refer to 50% or more, 55% or more, 60% or more, 65% or more, 70% or more, 75% or more, 80% or more, 85% or more, 90% or more, 95% or more, 97% or more, 98% or more, 99% or more, or 100% of something is removed (e.g., an artifact is removed from a recorded signal).

As used herein, the term "body" can refer to one or more neural structures being studied in vivo.

As used herein, the term "preparation" can refer to one or more neural structures being studied in vitro.

II. Overview

Neural recordings can acquire electrical potentials that can be generated in response to application of an electrical signal to one or more neural structures. Often the acquired electrical potentials can be distorted by an artifact due to interference of the applied electrical signal with the recorded electrical potentials. Traditionally, the artifact can be removed by amplifier blanking or post-hoc data manipulation, but these classical approaches lead to irreversible loss of signal. Filters were also used classically to reduce the artifact. Contrary to classical approaches, the present disclosure sets forth systems and methods to eliminate artifacts due to delivery of an electrical signal from neural recordings without the irreversible signal loss characteristic of the blanking period and the post-hoc data manipulation and without relying on the, often inadequate, filters.

The stems and methods utilize one or more separate electrodes to inject a counter stimulus (CS) applied anywhere in the body or preparation, as long as it is not activating any neural structures, and designed with parameters chosen to cancel out an activating stimulus (AS) (the electrical signal applied to the neural structure). For example, the parameters can be timing and/or amplitude parameters, which may be individually controlled to lead to the CS being inverted from the AS, out of phase with the AS (e.g., 180 degrees out of phase), or the like. The parameters can lead to the CS being received at the recording input of the recording electrode at the same time as the AS, thereby reducing the stimulus artifact amplitude seen by the recording electrode and, therefore, by the recording amplifier.

III. Systems

An aspect of the present disclosure can include a system 10 (FIG. 1) that can eliminate artifacts due to delivery of an electrical signal (e.g., for neural stimulation or nerve block) from neural recordings. The electrical signal that causes the artifact is referred to herein as an "activating stimulus" (AS). A signal that can be used to eliminate the artifact is referred to herein as the "counter stimulus" (CS). The neural recordings can include electrical potentials that be obtained from the neural structure and/or a muscle associated with the neural structure as the response to deliberate electrical stimulation of a neural structure with the AS. The electrical potentials can include, for example, electromyogram (EMG) signals, electroneurogram (ENG) signals, or the like. For example, when a blocking signal is delivered to a nerve, the electrical potentials can include one or more compound action potentials (CAPs).

The system 10 includes one or more waveform generators 11 to generate electrical waveforms. As shown in FIG. 1, the one or more waveform generators 11 can include an AS generator 12 and a CS generator 13 (in FIG. 1 the AS generator 12 and CS generator 13 are illustrated as separate devices; however, it should be noted that the AS generator 12 and the CS generator 13 can be part of a same device). The AS generator 12 can be configured to generate the AS as an electrical waveform with a feature configured to stimulate or block conduction in a neural structure. The CS generator 13 can be configured to generate the CA as an electrical waveform with at least one of a timing parameter (e.g., a phase shift based on conduction time through neural tissue) and an amplitude parameter (as well as other parameters, in some instances) selected based on the feature of the AS. As an example, the feature of the AS can contribute to an artifact, such as an amplitude, a timing, a shape, a phase, a frequency, or the like. In some instances, the AS generator 12 and CS generator 13 can configure and deliver voltage waveforms. In other instances, the AS generator 12 and CS generator 13 can configure and deliver current waveforms. In either instance, one or more additional circuit elements may be present before the waveform is delivered to respective electrodes (e.g., amplifiers, filters, convertors, (I to V or V to I), etc.).

The system 10 can also include at least one neural electrode (NS(S)) 15, which can be placed at a first position to be located at a first location. In some instances, the first position can be proximal to one or more neural structures being studied either in vitro (within a preparation) or in vivo (within a body). The first position can be chosen to deliver the AS to the neural structure to affect conduction in the neural structure based on the specific application (e.g., stimulation or block). The NE(S) 15 can be coupled to the AS generator 12 to receive the AS. The NE(S) 15 can thereafter deliver the AS to the one or more neural structures. As an example, the AS can be a kilohertz frequency alternating current (KHFAC) blocking waveform with a high amplitude. As another example, the AS can be a can be a stimulating waveform.

The system 10 can also include at least one counter electrode (CS(S)), which can be placed at a second position to be located at a second location. In some instances, the second position can be remote from one or more neural structures being studied either in vitro (within a preparation) or in vivo (within a body). The second position can be chosen such that the CS does not affect the conduction in the neural structure. For example, the second position can be within non-neural tissue. The CE(S) 16 can be coupled to the CS generator to deliver the CS to the second position.

Additionally, the system can include a recording device, which includes one or more recording electrodes (RE(S)) 17, a recorder 16, and, in some instances, additional circuitry (e.g., an amplifier, a filter, or the like). The RE(S) 17 can be placed at a third position to be located at a third location. In some instances, the third position can be closer to the second position than the first position so that the RE(S) 17 are closer to the CE(S) 15 than the NS(S) 13 either in vitro (within a preparation) or in vivo (within a body). The signal recorded by the RE(S) 17 at the third location and transmitted to the recorder 16 can be without artifact due to the AS (in other words, the artifact can be eliminated by the CS counteracting the artifact due to the AS, which may be due to the CS cancelling out at least a portion of the AS and/or the artifact). In some instances, the recorder 16 can send the electrical potentials as feedback (e.g., to the CS generator 13, which can utilize the feedback to configure the CS and/or to the AS generator 12, which can utilize the feedback to configure the AS).

IV. Methods

Figure 2:
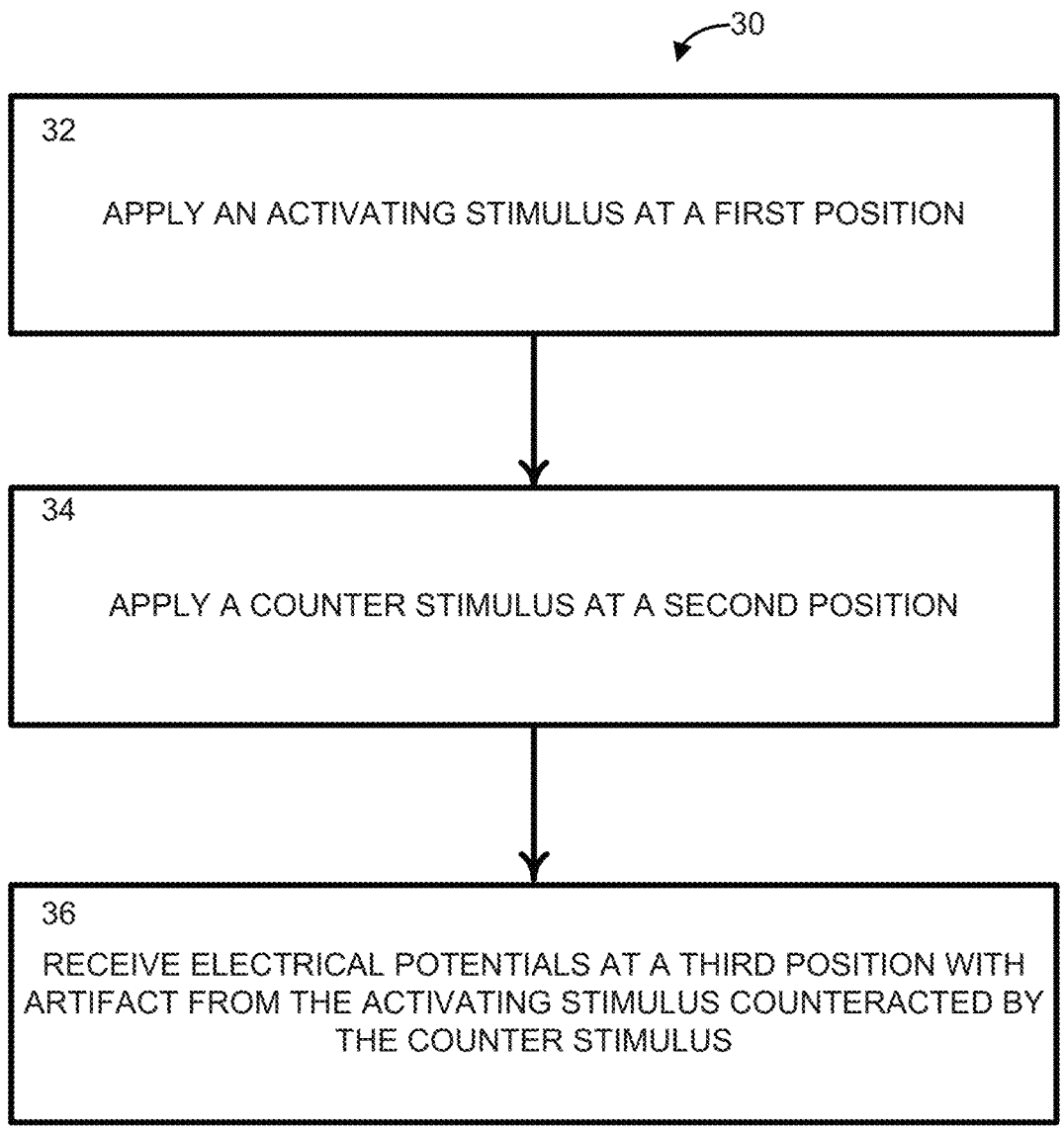
FIG. 2 is a process flow diagram illustrating a method for eliminating artifacts due to delivery of an electrical signal (e.g., for neural stimulation or nerve block) from neural recordings according to another aspect of the present disclosure.

Another aspect of the present disclosure can include a method 20 for eliminating artifacts due to delivery of an electrical signal (e.g., for neural stimulation or nerve block) from neural recordings, as shown in FIG. 2. The methods 20 can be executed using the system 10 shown in FIG. 1, for example, the deliver a counter stimulus (CS) to counteract an artifact due to an activating stimulus (AS) that can corrupt the neural recordings.

For purposes of simplicity, the method 20 is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method 20.

At Step 32, an activating stimulus (AS) (e.g., generated by AS generator 12) can be applied (e.g., by NE(S) 14) at a first position. The first position can be within a body or a preparation proximal to a neural structure. The AS includes an electrical waveform configured to affect (e.g., stimulate or block) conduction in the neural structure. The AS can have a feature (e.g., the feature can be an artifact that may be generated upon application of the AS). In some instances, an additional step of the method can include inserting the NE(S) into the first position.

At Step 34, a counter stimulus (CS) (e.g., generated by CS generator 13) can be applied (e.g., by CE(S) 15) at a second position. The second position can be within a body or a preparation remote from the neural structure so not to affect conduction in the neural structure. For example, the second position can be within non-neural tissue. The CS can be configured with a timing parameter and an amplitude parameter, as well as any other relevant parameters, selected based on the feature of the AS. In some instances, an additional step of the method can include inserting the CE(S) into the second position.

At Step 36, electrical potentials (e.g., in response to application of the AS) can be received (by RE 17) at a third position. The electrical potentials can be, for example, electromyogram (EMG) data or electroneurogram (ENG) data. The third position can be within a body or a preparation proximal to the second position such that the third position is closer to the second position than the third position. In some instances, an additional step of the method can include inserting the RE(s) into the third position. The CS can counteract an artifact due to the AS such that the artifact is eliminated from the electrical potentials. In some instances, the CS can cancel out a portion of the AS and/or the artifact associated with the AS.

V. Examples

The following examples describe eliminating artifacts due to delivery of an electrical signal (e.g., for neural stimulation or nerve block) from neural recordings. The following examples are for the purpose of illustration only is not intended to limit the scope of the appended claims.

In Vitro

Artifacts can be eliminated from in vitro recordings.

Methods

Figure 3:
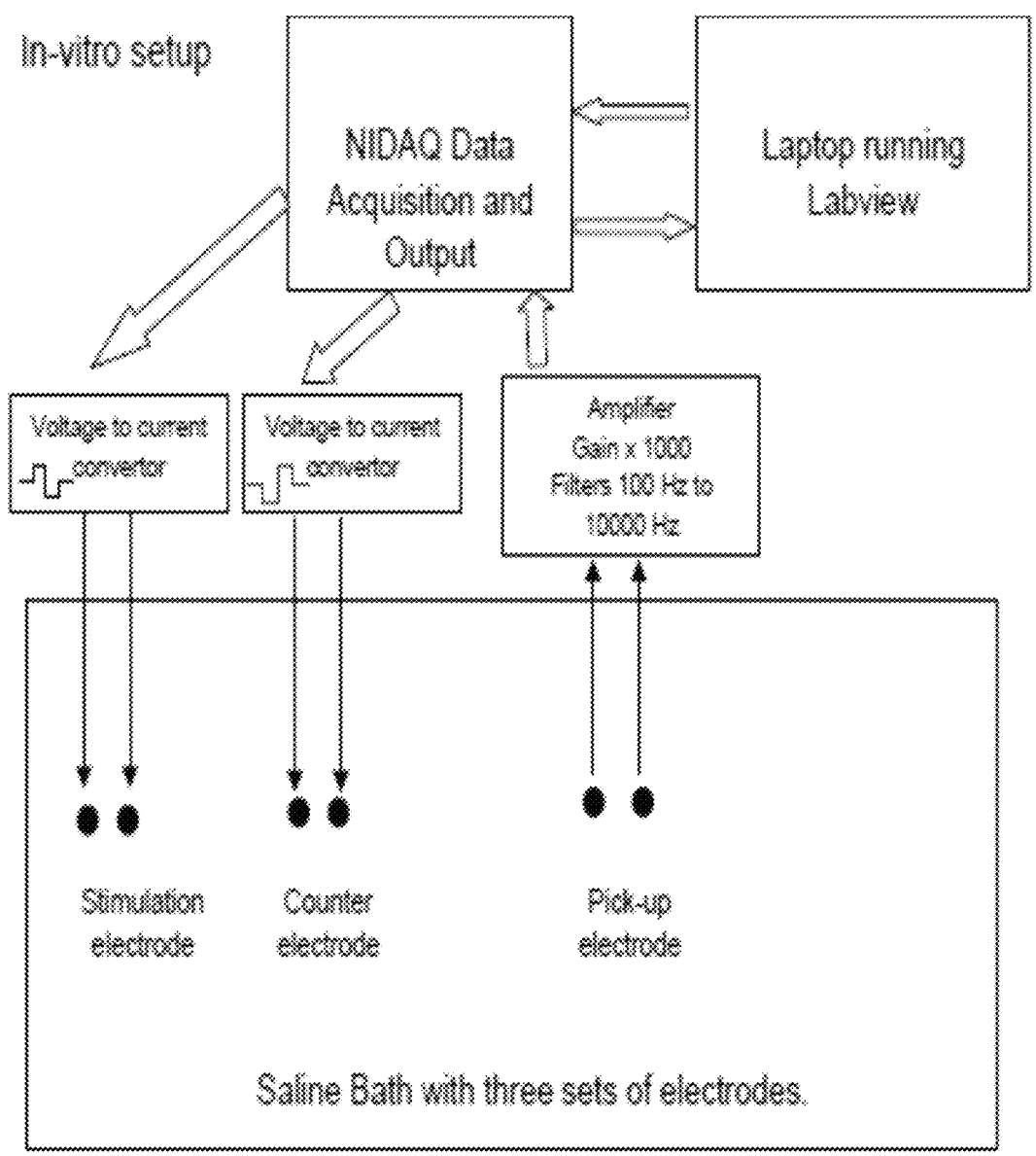
FIG. 3 shows a schematic of an example in vitro setup.

As shown in FIG. 3, a bipolar stimulation electrode can deliver a stimulus pulse and a bipolar counter electrode can deliver a counter pulse with an opposite polarity. The counter pulse can be configured (by a NIDAQ data acquisition and output system and/or a voltage to current converter and/or a laptop running LabVIEW) based on the stimulus pulse. A bipolar recording electrode (or "pick-up electrode") can be connected to an amplifier circuit, which can deliver the recording to a NIDAQ data acquisition and output system and the laptop running LabVIEW.

Results

Figure 4:
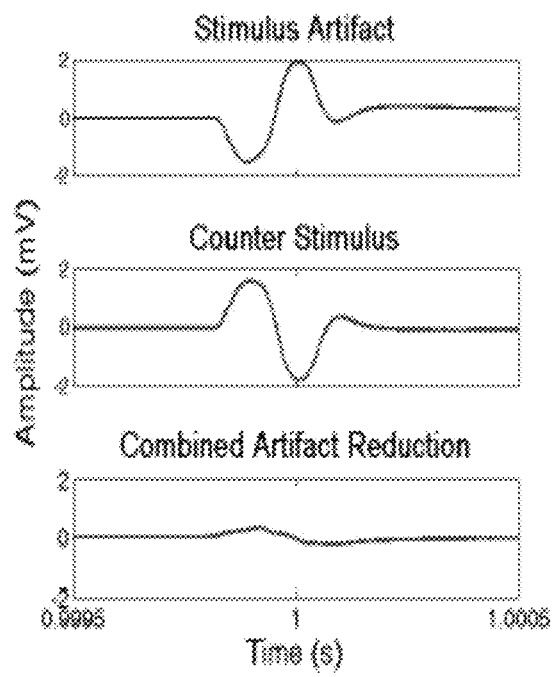
FIGS. 4 and 5 show example combined artifact reductions due to application of a counter stimulus specifically configured due to the activating waveform used.
Figure 5:
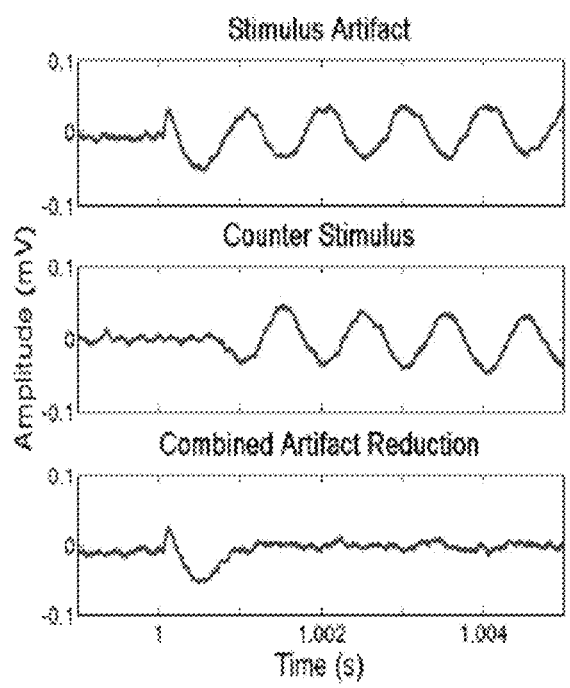

Example results are shown in FIGS. 4 and 5. The results in FIG. 4 are with a biphasic square stimulus pulse (the artifact looks like a sinusoidal due to the capacitance of the electrode); the counter stimulus (opposite polarity) reduces 80% of noise seen in the combined artifact reduction. FIG. 5 shows results with an injected sinusoidal kilohertz frequency altered current (KHFAC) with a 2 mA peak to peak at 1 kHz; the counter stimulus (phase shirted 180 degrees out of phase with the activating stimulus) reduces 85% of noise seen in the combined artifact reduction.

In Vivo

Artifacts can be eliminated from in vivo recordings.

Methods

Figure 6:
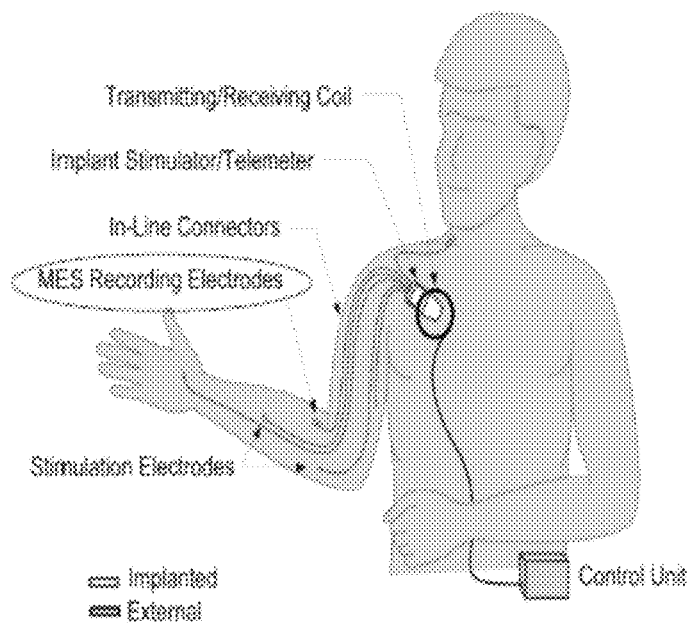
FIG. 6 shows an example of an implanted functional electrical system with implanted EMG electrodes, for which the counter stimulus can be used to remove nose from a detected EMG signal.

A functional electrical stimulation system with implanted EMG control electrodes is shown in FIG. 6. The stimulation electrodes, recording electrodes, and stimulation circuitry (implant stimulator/telemeter) can be implanted in the patient's body, while a control unit can be external to the patient's body. The control unit can have an external coil (transmitting/receiving coil) that is used for communication with an implanted coil on the stimulation circuitry (implant stimulator/telemeter). One or more counter electrodes can be located within the body. Recorded electromyogram (EMG) or electroneurogram (ENG) signals (recorded based on the stimulation) can be used as a command control source (to configure the stimulation).

In this example, the neural electrode (e.g., stimulating electrodes) and the counter electrode (remote from the nerve being stimulated) can be connected to a controller (the implant stimulator/telemeter) that includes a processor. The controller can be part of a neural stimulation system controlled by a feedback signal and used on a human subject.

Results

Figure 7:
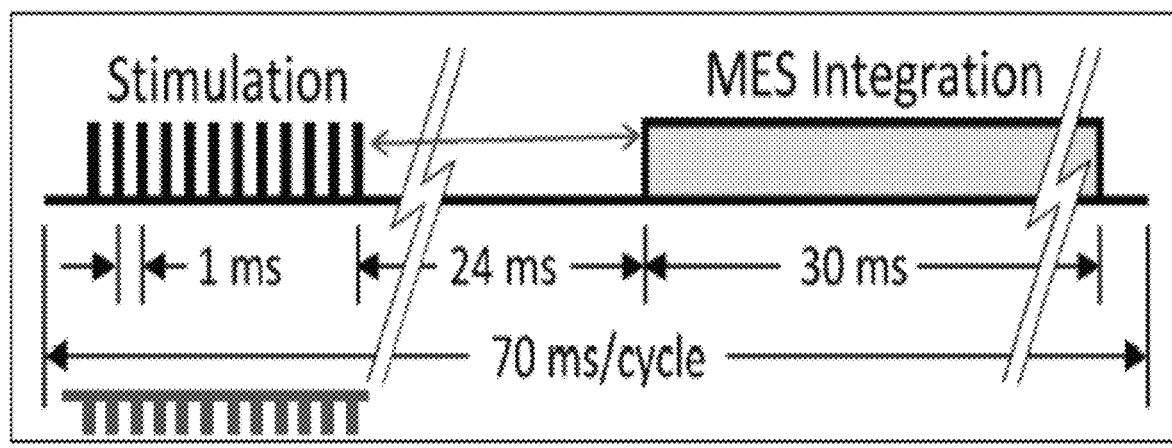
FIG. 7 shows an example of use of a specifically-configured counter stimulus to remove stimulation artifact from a detected EMG signal.

FIG. 7 shows the 24 ms gap were EMG cannot be obtained due to stimulation artifacts and the proposed injections of a counter stimulus (or counter pulses injected through a single electrode with amplitude adjustment of each pulse individually). The counter stimulus can reduce the artifact a considerable extent.

From the above description, those skilled in the art will perceive improvements, changes and modifications. Such improvements, changes and modifications are within the skill of one in the art and are intended to be covered by the appended claims.

The following is claimed:

1. A method comprising:
   applying an activating stimulus (AS), by at least one neural electrode located at a first position within a body or a preparation proximal to a neural structure, at the first position, wherein the AS comprises an electrical waveform configured to affect conduction in the neural structure;
   applying a counter stimulus (CS), by at least one electrode located at a second position within the body or the preparation remote from the neural structure, at the second position, wherein the CS comprises an electrical waveform configured with a timing parameter and an amplitude parameter selected based on a feature of the AS, wherein the timing parameter leads to the CS being phase shifted from the AS based on conduction time through the neural structure so that the CS cancels out at least a portion of the AS; and
   receiving, by at least one recording electrode located at a third position within the body or the preparation, electrical potentials from the body or the preparation, wherein the third position is near the second position and wherein the CS counteracts an artifact caused by the AS at the third location.

2. The method of claim 1, wherein the feature of the AS is an amplitude.

3. The method of claim 2, wherein the AS is a kilohertz frequency alternating current (KHFAC) blocking waveform with a high amplitude that overwhelms data within the electrical potentials, wherein the data comprises compound action potentials (CAPs).

4. The method of claim 2, wherein the amplitude is a stimulus artifact amplitude.

5. The method of claim 1, further comprising
   inserting the at least one neural electrode at the first position within the body or the preparation proximal to the neural structure; and
   inserting the at least one electrode at the second position within the body or the preparation remote from the neural structure, wherein the second position is within non-neural tissue.

6. The method of claim 1, wherein the at least one neural electrode in the first position within the body or the preparation is configured to stimulate the neural structure to stimulate conduction and/or block conduction in the neural structure.

7. The method of claim 1, wherein the at least one neural electrode and the at least one electrode are connected to a controller comprising a processor, wherein the controller is part of a neural stimulation system controlled by a feedback signal and used on a human subject.

8. The method of claim 1, wherein the AS and the CS are each delivered to an animal subject used for research, wherein the electrical potentials comprises electromyogram (EMG) data or electroneurogram (ENG) data.

9. A system comprising:
   at least one waveform generator configured to generate an activating stimulus (AS), comprising a first electrical waveform comprising a feature, and a counter stimulus (CS), comprising a second electrical waveform configured with a timing parameter and an amplitude parameter selected based on the feature of the AS, wherein the timing parameter leads to the CS being phase shifted from the AS based on conduction time through the neural structure so that the CS cancels out at least a portion of the AS;
   at least one neural electrode coupled to the at least one waveform generator to receive the AS and configured to be placed in a first position within a body or a preparation proximal to a neural structure to deliver the AS to the neural structure to affect conduction in the neural structure;
   at least one electrode coupled to the at least one waveform generator to receive the CS and configured to be placed in a second position within the body or the preparation remote from the neural structure to deliver the CS to the second position; and
   a recording device comprising a recording electrode configured to be placed at a third position within the body or the preparation to receive electrical potentials from the neural structure, wherein the third position is near the second position and wherein the CS counteracts an artifact caused by the AS at the third location.

10. The system of claim 9, wherein the recording device utilizes the electrical potentials as feedback to configure the AS and/or the CS.

11. The system of claim 9, wherein the feature of the AS is an amplitude.

12. The system of claim 11, wherein the AS is a kilohertz frequency alternating current (KHFAC) blocking waveform with a high amplitude, wherein the electrical potentials comprise compound action potentials (CAPs).

13. The system of claim 11, wherein the amplitude is a stimulus artifact amplitude.

14. The system of claim 9, wherein the at least one neural electrode in the first position within the body or the preparation is configured to stimulate the neural structure to stimulate conduction and/or block conduction in the neural structure.

15. The system of claim 9, wherein the at least one waveform generator comprises a first waveform generator configured to generate the AS and a second waveform generator configured to generate the CS.

16. The system of claim 9, wherein the electrical potentials comprises electromyogram (EMG) data or electroneurogram (ENG) data.

* * * * *